(12) United States Patent
Pflanz et al.

(10) Patent No.: US 11,426,696 B2
(45) Date of Patent: Aug. 30, 2022

(54) CONNECTION DEVICE FOR A SUCTION APPARATUS OF A VACUUM DIAPHRAGM FILTER

(71) Applicant: SARTORIUS STEDIM BIOTECH GMBH, Goettingen (DE)

(72) Inventors: Karl Pflanz, Goettingen (DE); Sebastian Pruehl, Goettingen (DE); Michael Schuetzler, Goettingen (DE); Juliane Grossmann, Goettingen (DE)

(73) Assignee: SARTORIUS STEDIM BIOTECH GMBH, Goettingen (DE)

( * ) Notice: Subject to any disclaimer, the term of this patent is extended or adjusted under 35 U.S.C. 154(b) by 219 days.

(21) Appl. No.: 16/767,070

(22) PCT Filed: Oct. 11, 2018

(86) PCT No.: PCT/EP2018/077789
§ 371 (c)(1),
(2) Date: May 26, 2020

(87) PCT Pub. No.: WO2019/101428
PCT Pub. Date: May 31, 2019

(65) Prior Publication Data
US 2020/0368689 A1 Nov. 26, 2020

(30) Foreign Application Priority Data
Nov. 27, 2017 (DE) .................... 10 2017 127 969.5

(51) Int. Cl.
*B01D 61/20* (2006.01)
*B01D 63/08* (2006.01)
*C12M 1/12* (2006.01)

(52) U.S. Cl.
CPC .......... *B01D 61/20* (2013.01); *B01D 63/087* (2013.01); *C12M 37/02* (2013.01); *B01D 2313/16* (2013.01); *B01D 2313/24* (2013.01)

(58) Field of Classification Search
CPC .......... B01D 2201/204; B01D 2313/08; B01D 2313/16; B01D 2313/18; B01D 2313/24;
(Continued)

(56) References Cited

U.S. PATENT DOCUMENTS 5,375,477 A 12/1994 Neill et al.
5,529,694 A * 6/1996 Strickler ............ G01N 33/1833
422/89

(Continued)

FOREIGN PATENT DOCUMENTS

CN 102586082 A 7/2012
DE 3139571 A1 4/1983
(Continued)

OTHER PUBLICATIONS

International Search Report, Application No. PCT/EP2018/077789, dated Feb. 12, 2019, 2 pages.

*Primary Examiner* — Pranav N Patel
(74) *Attorney, Agent, or Firm* — Dilworth IP, LLC

(57) ABSTRACT

A connection mechanism for a suction device for vacuum membrane filtration applications, includes a support for receiving a membrane filter or a filtration base, a cavity formed below the membrane filter or the filtration base, a suction duct which opens centrally into the cavity, and a ventilation duct which opens laterally into the cavity. The connection mechanism further includes a closing element which can be moved into several switching positions and which can block or unblock both the suction duct and the ventilation duct depending on the switching positions.

16 Claims, 3 Drawing Sheets

(58) Field of Classification Search
CPC .. B01D 2315/08; B01D 29/05; B01D 29/085; B01D 61/18; B01D 61/20; B01D 63/087; C12M 37/02; G01N 2001/4088
See application file for complete search history.

(56) References Cited

U.S. PATENT DOCUMENTS

| | | |
|---|---|---|
| 5,603,900 A | 2/1997 | Clark et al. |
| 6,623,631 B1 | 9/2003 | Graus et al. |
| 2007/0144959 A1 | 6/2007 | Zuk, Jr. |
| 2010/0000933 A1 | 1/2010 | Zuk, Jr. |

FOREIGN PATENT DOCUMENTS

| | | |
|---|---|---|
| DE | 19513969 A1 | 9/1995 |
| DE | 19905645 C1 | 10/2000 |
| DE | 69633029 T2 | 7/2005 |
| EP | 1556152 B1 | 7/2005 |
| WO | 2015032464 A2 | 3/2015 |

* cited by examiner

CONNECTION DEVICE FOR A SUCTION APPARATUS OF A VACUUM DIAPHRAGM FILTER

The invention relates to a connection means for a suction device for vacuum membrane filtration applications.

BACKGROUND OF THE INVENTION

In the context of microbiological-hygienic analyses of aqueous samples, the so-called membrane filter method is usually applied, in which a membrane filter having a suitable pore size is placed in a filtration device and the sample is filtered so that the microorganisms contained in the test material are retained on the filter surface by the retention effect of the membrane filter. Contaminations present in liquid media are generally low, which is why the test typically requires sample quantities of more than 100 ml.

In well-known vacuum membrane filtration devices for the microbiological analysis of liquid media, the filtration device consists of a filtration base, a membrane filter (preferably having a diameter of 47 to 50 mm) and a funnel for pouring the liquid sample. In most applications, the filtration devices are mounted on reusable stainless steel suction strips, by means of which a negative pressure (hereinafter referred to as vacuum for simplicity) carries the filtrate to the pump. Furthermore, a culture medium is required with which the filter is brought into contact after filtration. Typical for this are petri dishes in various sizes (preferably having a diameter of approx. 55 mm).

While the suction strip, the filtration base and the membrane filter remain unchanged for these samples, the size of the infusion funnel is mostly adapted to the volume of the medium to be analyzed. Therefore, systems in which different versions of the funnel are suitable for the same accommodation or filtration base are advantageous.

The filtration base and the infusion funnel are available as stainless steel units, and in various design forms also in plastic. In the latter case, they are usually available pre-sterilized and are intended for use as single-use units. In all handling steps, the preservation of sterility of the aids used are in the foreground, as otherwise the product and/or the diagnostic result would be falsified.

For stainless steel designs, the membrane filter must basically be inserted separately between the infusion funnel and the filtration base. To ensure sterility, the insertion is typically performed by means of heat-sterilized tweezers. The removal of the membrane filter for subsequent analyses is again performed using tweezers re-sterilized by heat.

There are also various plastic membrane filtration devices in which the membrane filter is already inserted and the complete device is provided in a sterile state. Here, the task of inserting the membrane filter into the filtration device is not necessary.

As already mentioned, in most applications, the filtration devices are mounted on reusable stainless steel suction strips via which the vacuum carries the filtrate to the pump. As the side facing away from the membrane filter is directly connected to the vacuum source and to other lines and receptacles, these areas are considered as non-sterile. Usually, the side facing away from the filtration is not disinfected before each filtration, either. This is mostly carried out only at the end of the day, e.g. overnight.

During vacuum membrane filtration, a vacuum is applied to the side facing away from the filtration, which is not broken even after the filtration is completed. As long as there is no ventilation between the membrane filter and the filtrate, the residual liquid cannot flow off. However, ventilation is blocked by the wetted membrane filter.

It is difficult to remove the wetted membrane filter when a vacuum is applied, which is why in various systems on the market, the vacuum is broken via the suction strip or the pump unit. However, as a vacuum cavity is applied directly below the filtration base, the residual amount of filtrate that has not flown off can be sprayed up. During this process, back-contaminations are generated by splashing water.

Under the product name Combisart®, vacuum membrane filtration systems marketed by the Applicant are known, which have a stainless steel suction strip which provides connection options for several filter stations. Each of the filter stations can be ventilated in a sterile manner via the respective connection of the suction strip in order to exclude a secondary contamination of the bottom side of the filter during ventilation. It is possible to switch between a vacuum position and a ventilation position using an operating element. In the vacuum position, a suction duct is unblocked which opens centrally below the horizontally arranged membrane filter. The liquid substance contained in the respective filter station is sucked in through the membrane filter via the suction duct. In the ventilation position, a closing element blocks the suction duct and simultaneously unblocks a ventilation duct in that the closing element establishes a flow communication between a separate ventilation passage and the upper part of the suction duct. The ventilation duct is thus formed by the ventilation passage and the upper part of the suction duct, which opens centrally below the membrane filter.

Furthermore, documents EP 1 556 152 B1 and CN 102586082 A, for example, disclose negative pressure drainage means for filtration devices having a suction duct which opens onto a receiving surface of a mechanical support facing the membrane filter in order to suck the liquid substance contained in the filtration device through the membrane filter. For ventilation, a ventilation duct completely separated from the suction duct is respectively provided here, which can be closed and opened using a separate valve.

SUMMARY OF THE INVENTION

The object of the present invention is to simplify the ventilation of the area below the membrane filter necessary to prevent recontaminations, in particular by means of a connection means which does not require complicated valves or electrical actuators and can be implemented with a few device parts which can be easily assembled and disassembled, are easy to clean and adapted to be sterilized.

This object is achieved by a connection means for a suction device for vacuum membrane filtration applications including a support for receiving a membrane filter or a filtration base, a cavity formed below the membrane filter or the filtration base, a suction duct which opens centrally into the cavity, and a ventilation duct which opens laterally into the cavity, characterized by a closing element which can be moved into several switching positions and which can block or unblock both the suction duct and the ventilation duct depending on the switching positions. Advantageous and useful configurations of the connection means according to the invention are specified in the subclaims.

The connection means according to the invention for a suction device is provided for vacuum membrane filtration applications and comprises a support for receiving a membrane filter or a filtration base, a cavity formed below the membrane filter or the filtration base, a suction duct which opens centrally into the cavity, and a ventilation duct which opens laterally into the cavity. According to the invention, the connection means further comprises a closing element which can be moved into several switching positions and which can block or unblock both the suction duct and the ventilation duct depending on the switching positions.

The invention is based on the findings that additional components can be saved in a connection means if the closing element is configured such that it is adapted to unblock or block not only the suction duct but at the same time the ventilation duct alone in the respective switching positions, i.e. independently of further adjustment elements. An additional valve or the like for selective unblocking of the ventilation duct can therefore be omitted. The closing element which can be moved into the different switching positions can be designed such that when the switching position is changed, the movement of the closing element alone sets the suction duct and simultaneously the ventilation duct into the state corresponding to the switching position (unblocked or blocked). Due to the absence of an additional adjusting element for the ventilation duct, the structure of the connection means according to the invention is simplified, the manufacture of the latter being accordingly cost-effective.

The connection means according to the invention, if ventilation is desired, is able to reduce the vacuum present in the suction duct below the membrane filter or to create a pressure compensation with respect to the environment, so that the filtrate cannot splash back to the bottom side of the membrane filter and at the same time residual liquid below the membrane filter is sucked off.

The ventilation duct should open as far up as possible into the cavity below the membrane filter in order to effectively prevent any liquid present in the cavity or splashing up from entering the ventilation duct. Accordingly, in a preferred embodiment of the invention, the ventilation duct opens above a collecting part of the cavity. A collecting part is to be understood here as that lower area of the cavity below the membrane filter in which (residual) liquid may be present during or after completion of a filtration process. The inlet of the ventilation part is thus higher than the liquid level of the (residual) liquid, as it is typically found during or after a filtration process.

In the connection means according to the invention, the ventilation duct is preferably separated from the suction duct in each switching position, i.e. there is never a direct flow communication between the ventilation duct and the suction duct—unlike, for example, in the Combisart® vacuum membrane filtration systems. The continuous separation allows the suction duct and the ventilation duct to be designed in accordance with the respective requirements without having to make any compromises. The decisive advantage, however, is that the suction duct and the pressure duct can be unblocked or blocked independently of each other by the closing element. This is possible, in particular, due to the switching position desired for pressure compensation below the membrane filter with simultaneous aspiration of the residual liquid, in which both the suction duct and the pressure duct are unblocked.

In a preferred embodiment of the invention, the closing element has both at least one suction duct part to complete the suction duct in at least one switching position and at least one ventilation duct part to complete the ventilation duct in at least one switching position. By a suitable movement of the switching element, these duct parts can be brought into position so that the suction duct or the ventilation duct or both are completed and thus unblocked.

The connection means according to the invention has at least two, ideally three different switching positions:

In a first switching position, the suction duct is unblocked and the ventilation duct is blocked. This corresponds to a "vacuum" position in which filtration operation takes place and no simultaneous ventilation is desired.

In a second switching position, both the suction duct and the ventilation duct are unblocked. This corresponds to a "ventilation" position, in which after completion of a filtration, the vacuum still applied to the suction duct ensures that the residual liquid is sucked off without splashing up.

In a third switching position, the suction duct is blocked and the ventilation duct is unblocked. This corresponds to a "stop" position, in which no filtration operation is provided but ventilation is useful or desired to facilitate the removal of the membrane filter or the filtration base from the support.

Concerning the suction duct, the most simple way to achieve the aforementioned switching positions is to form two suction duct parts in the closing element, one of which completes the suction duct in the first switching position ("vacuum") and the other completes the suction duct in the second switching position ("ventilation").

With regard to the ventilation duct, the simplest way to achieve the switching positions is to form two ventilation duct parts in the closing element, one of which completes the ventilation duct in the second switching position ("ventilation") and the other completes the ventilation duct in the third switching position ("stop").

Particularly preferred is an embodiment of the invention in which the closing element is rotatably mounted in a body of the connection means in which the support is also inserted. A rotation of the closing element into the different switching positions, if necessary using an operating element acting on the closing element, is a switching movement which can be easily and intuitively performed by the operator. In addition to the rotatable mounting of the closing element, the body of this embodiment also fulfils a further function by serving as a accommodation for the support of the connection means.

The body of the connection means, into which the support is inserted, is preferably made of stainless steel or aluminum and is firmly or detachably connected to a suction device, which is typically also made of stainless steel or aluminum.

The closing element is preferably detachably mounted in the body. As the closing element can wear out due to its mobility and the contact with the medium, it is useful to design it as a replaceable part.

In the structure described above of the connection means with a body in which the closing element is rotatably mounted and a support that is firmly but detachably inserted into the body, it is necessary for the ventilation duct to have a ventilation duct part in the body and a ventilation duct part in the support. The body and the support are typically configured so as to be essentially rotationally symmetrical. In order to avoid the need to obligatorily insert the support in a specific rotational position relative to the body such that the ventilation duct parts are aligned with each other, a preferred embodiment provides a sealed cavity formed substantially annularly between the body and the support. This cavity which is sealed for example by O-rings ensures in any case a flow communication between the ventilation duct part of the body and the ventilation duct part of the support, irrespective of the rotational position.

Particularly with regard to simple operation, it is useful to configure the connection means as a stopcock having a closing element in the form of a plug (conical shut-off body).

According to invention, the different switching positions are achieved by moving the closing element into appropriate positions. It is therefore advantageous to mechanically couple the closing element to an operating element so that the user can switch between the switching positions without any difficulty.

Preferably, the connection means according to the invention is provided with a latching mechanism for the closing element, which holds the closing element in the respective switching position in a defined manner.

In order to prevent a contamination of the bottom side of the membrane filter during ventilation, a sterile air filter should be connected upstream of the ventilation duct of the connection means.

BRIEF DESCRIPTION OF THE DRAWINGS

Further features and advantages of the invention will become apparent from the description below and from the attached drawings, to which reference is made and in which.

DETAILED DESCRIPTION OF THE INVENTION

Figure 1B:
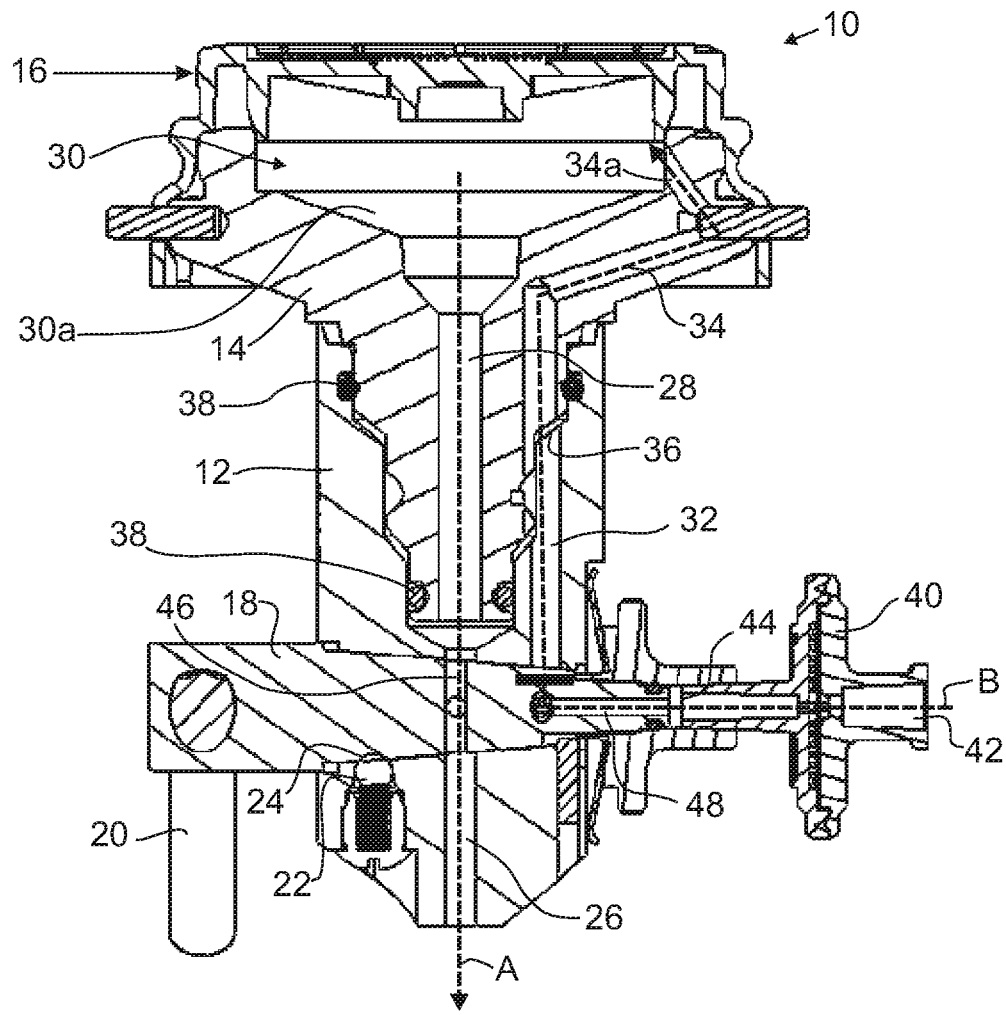
FIGS. 1a and 1b show a lateral external view and a lateral sectional view rotated by 90° of a connection means according to the invention for a suction device in a first switching position ("vacuum")
Figure 1A:
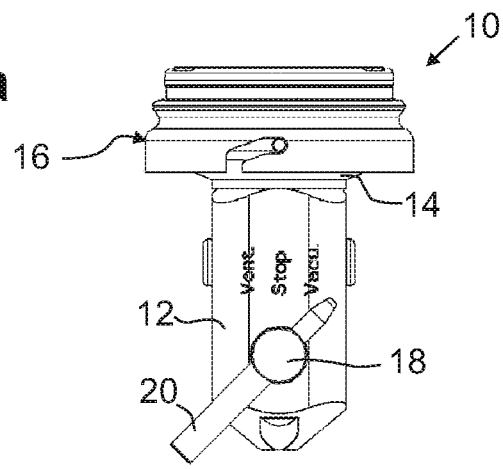

FIGS. 1a and 1b show a connection means 10 made of stainless steel for a suction device provided for vacuum membrane filtration applications.

The connection means 10 comprises an elongated body 12 into which a support 14 is inserted. In the inserted state, the support 14 is firmly and tightly connected to the body 12, but can also be removed from the body 12. This is important with regard to a cleaning of the connection means 10 and the possibility of inserting different supports 14 into the body 12.

A filtration base 16 is placed on the support 14. For vacuum membrane filtration, an infusion funnel is mounted onto the filtration base 16, a membrane filter being clamped between the filtration base 16 and the funnel.

Below the support 14, a closing element 18 is rotatably mounted in the body 12, the longitudinal axes of the body 12 and of the support 14 extending concentrically and vertically to the horizontal axis of rotation of the closing element 18. The closing element 18 is configured as a truncated plug and is part of a stopcock. Various duct parts are formed in the closing element 18, which will be described in more detail later in the explanation of the functioning. The stopcock also includes a operating element 20, which acts outside the body 12 on the closing element 18, for manual operation of the closing element 18.

The closing element 18 can be rotated into at least two, in the example embodiment shown into three different stable switching positions by means of the operating element 20. A latching mechanism having a latching element 22 arranged in body 12 and pre-tensioned in the direction of the closing element 18 is provided for this purpose. The latching element 22 can engage in a known manner in individual latching recesses 24, which are formed in the closing element 18 and define the individual switching positions.

Central suction duct parts 26 and 28 which form the essential parts of a suction duct are formed on both sides of the closing element 18 in the body 12 and in the support 14. The first suction duct part 26 in the body 12 opens on the side facing away from the closing element 18 into a suction duct of a stainless steel suction strip which is not shown. The second suction duct part 28 in the support 14 opens on the side facing away from the closing element 18 centrally into a cavity 30 located below the filtration base 16 to be inserted. A lower part of this cavity 30, in which (residual) liquid may be present during or after completion of a filtration process, is referred to as collecting part 30a.

Ventilation duct parts 32 and 34, respectively, which are in flow communication with each other and form parts of a ventilation duct are formed in the body 12 and in the support 14 independently of the suction duct parts 26, 28. The flow communication between the two ventilation duct parts 32 and 34 can be established in that they include opposite openings aligned with each other, which however requires a specific rotational position of the support 14 relative to the body 12. In the example embodiment shown, a substantially annularly circumferential cavity 36 is therefore provided between the body 12 and the support 14, into which an opening of the ventilation duct part 32 formed in the body 12 and an opening of the ventilation duct part 34 formed in the support 14 open. The cavity 36 is sealed, in the example embodiment shown, by two O-rings 38 arranged at different axial heights between the body 12 and the support 14. Due to the circumferential cavity 36, the flow communication between the two ventilation duct parts 32 and 34 is always ensured, regardless of the rotational position of the support 14 relative to the body 12.

The end of the upper ventilation duct part 34 in the support 14 facing away from the lower ventilation duct part 32 opens laterally into the cavity 30 below the filtration base 16 to be inserted. The inlet 34a is located above the collecting part 30a of the cavity 30 at an axial height which—under normal circumstances—is above the liquid level of a (residual) liquid present in the cavity 30 during or after filtration.

The lower ventilation duct part 32 in the body 12 leads to the enveloping surface of the closing element 18.

The ventilation duct also includes a sterile air filter 40 arranged laterally on the body 12—here in extension of the axis of rotation of the closing element 18. The sterile air filter 40 has an inlet 42, which is in contact with the environment, and an outlet 44, which faces the end face of the closing element 18 facing away from the operating element 20.

According to an alternative embodiment which is not shown, the sterile air filter 40 can also be located at another point laterally on the body 12. In this case, the outlet 44 of the sterile air filter 40 faces the side wall of the body 12. For example, the sterile air filter 40 can be arranged offset at an angle of 90° with respect to the vertical center axis in the illustration of FIG. 1b, so that the flow path through the sterile air filter 40 is not in the paper plane but perpendicular to the paper plane.

In the following, the functioning of the connection means 10 will be explained with reference to the three switching positions shown in FIGS. 1a, 1b and 2a, 2b as well as 3a, 3b.

FIGS. 1a and 1b show the connection means 10 in a first switching position, which is referred to as "vacuum" in the following. The switching position "vacuum" corresponds to the intended operation of the connection means 10, if the medium contained in the inserted filtration base 16 is to be sucked through the membrane filter. Accordingly, the suction duct is unblocked in this switching position, which is symbolized by the uninterrupted arrow A indicating the suction direction. The suction duct is unblocked in the "vacuum" switching position as a third suction duct part 46 in the closing element 18 connects the first suction duct part 26 in the body 12 to the second suction duct part 28 in the support 14.

In contrast thereto, the ventilation duct is blocked by the closing element 18 in the "vacuum" position, as will be explained below. The outlet 44 of the sterile air filter 40 facing the closing element 18 opens into a horizontal third ventilation duct part 48 in the closing element 18. The third ventilation duct part 48 runs along the axis of rotation of the closing element 18 so that it is always in flow communication with the outlet 44 of the sterile air filter 40, irrespective of the rotational position of the closing element 18. In the "vacuum" position, however, no ventilation duct part branching off from the third ventilation duct part 48 in the closing element 18 is in flow communication with the second ventilation duct part 32 in the body 12. Therefore, no air from the environment can enter the part of the ventilation duct which opens into the cavity 30. This is symbolized by the crossbar in the closing element 18, which interrupts the arrow B.

In the case of the alternative arrangement of the sterile air filter 40 on the side of the body 12 which is not shown, the third ventilation duct part 48 is formed in the body 12 rather than in the closing element 18, so that the outlet 44 of the sterile air filter 40 opens into the inlet of the third ventilation duct part 48. In the "vacuum" position, however, as described above, no ventilation duct part formed in the closing element 18 is in flow communication with the second ventilation duct part 32 in the body 12, so that the ventilation duct is blocked.

Figure 2B:
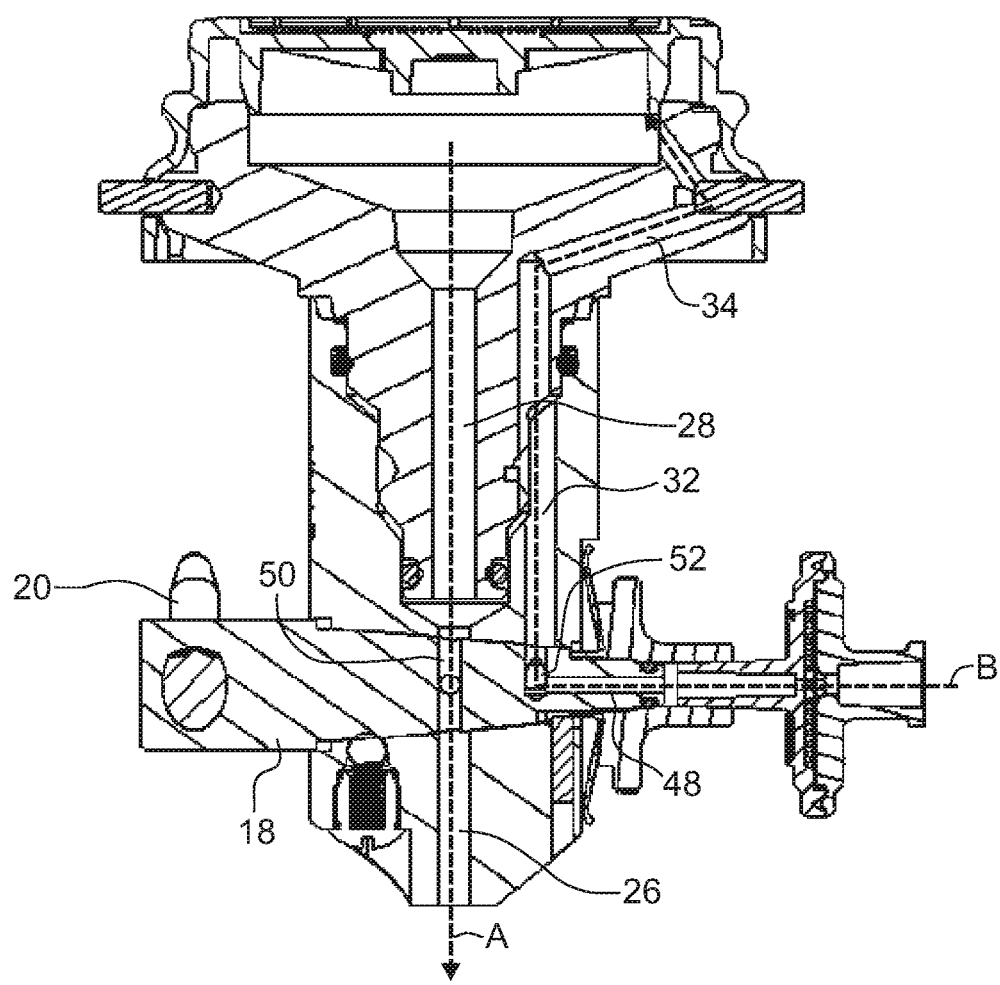
FIGS. 2a and 2b show a lateral external view and a lateral sectional view rotated by 90° of the connection means according to the invention in a second switching position ("ventilation")
Figure 2A:
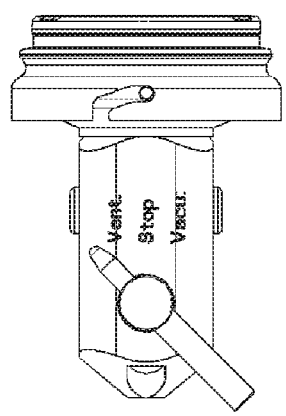

Starting from the "vacuum" position, the closing element 18 can be rotated counterclockwise to the "ventilation" ("vent.") switching position shown in FIGS. 2a and 2b using the operating element 20. In this switching position, both the suction duct and the ventilation duct are unblocked, as explained below.

In the "ventilation" switching position, a fourth suction duct part 50 in the closing element 18 connects the first suction duct part 26 in the body 12 to the second suction duct part 28 in the support 14, so that the suction duct is unblocked in accordance with the uninterrupted arrow A. (The fourth suction duct part 50 is not visible in the view of FIG. 1b due to the different rotational position of the clamping element 18).

At the same time, a further, fourth ventilation duct part 52 branching vertically off from the third ventilation duct part 48 in the closing element 18 establishes a flow communication between the third ventilation duct part 48 and the second ventilation duct part 32 in the body 12. (The fourth ventilation duct part 52 is not visible in the view of FIG. 1b due to the different rotational position of the closing element 18).

In the case of the alternative arrangement of the sterile air filter 40 on the side of body 12 which is not shown, the fourth ventilation duct part 52 in the closing element 18 establishes a flow communication between the third ventilation duct part 48 in the body 12 and the second ventilation duct part 32 in the body 12.

Thus, according to the uninterrupted arrow B, air from the environment can enter the cavity 30 laterally via the four ventilation duct parts 48, 52, 32, 34 after having passed through the sterile air filter 40.

The switching position "ventilation" serves to enable a safe aspiration of residual liquid without risk of recontamination after filtration with the vacuum still applied.

Figure 3B:
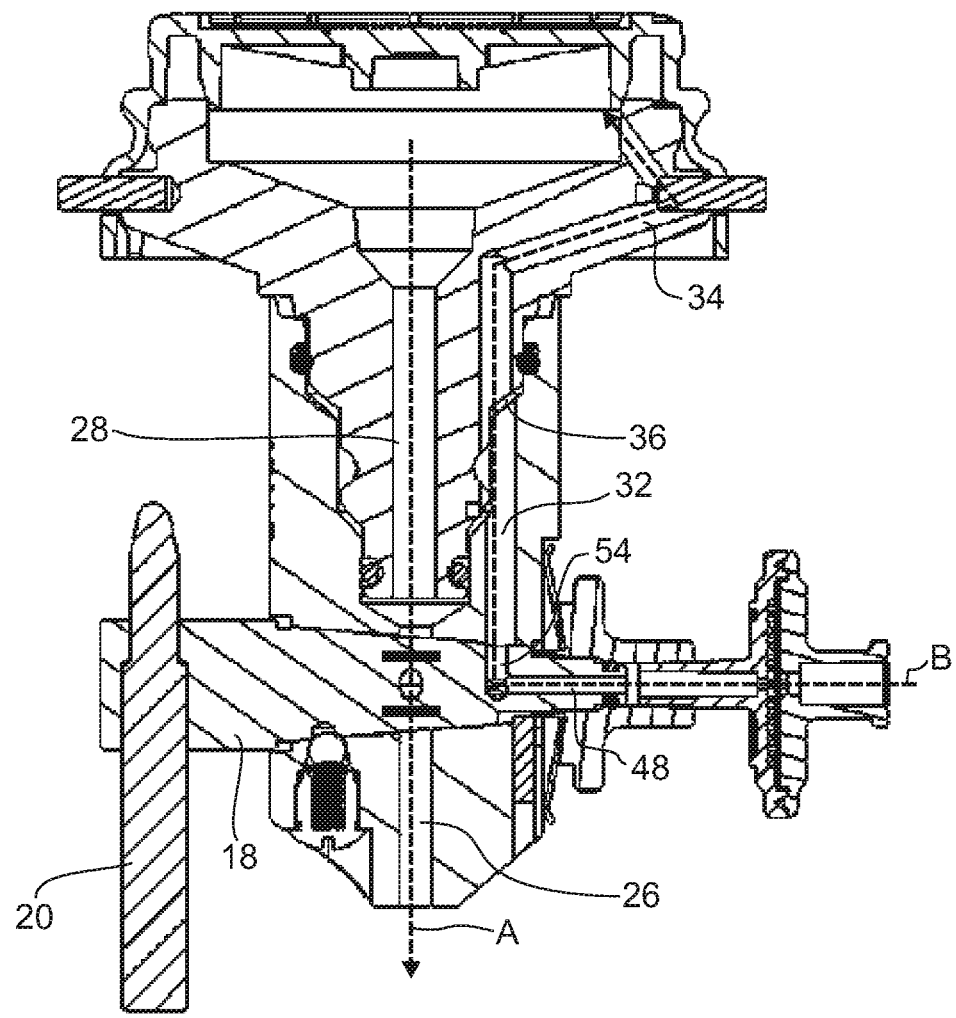
FIGS. 3a and 3b show a lateral external view and a lateral sectional view rotated by 90° of the connection means according to the invention in a third switching position ("Stop").
Figure 3A:
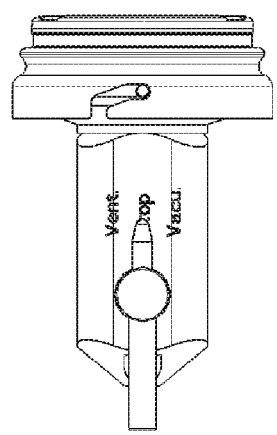

Finally, in order to permit a simplified removal of the wetted membrane filter, the closing element 18 is rotated clockwise from the "ventilation" switching position to the "stop" position by means of the operating element 20. In this switching position which is shown in FIGS. 3a and 3b, the suction duct is interrupted by the closing element 18 as neither the third suction duct part 46 nor the fourth suction duct part 50 establishes a flow communication between the first suction duct part 26 in the body 12 and the second suction duct part 28 in the support 14. This is symbolized by the two crossbars interrupting arrow A. Thus, a vacuum of the suction device still present at the lower mouth of the first suction duct part 26 has no effect on the membrane filter on the filtration base 16.

In the "stop" switching position, however, the ventilation duct is still unblocked as a fifth ventilation duct part 54 branching off from the third ventilation duct part 48 in the closing element 18 is in flow communication with the second ventilation duct part 32 in the body 12.

In the case of the alternative arrangement of the sterile air filter 40 on the side of body 12 which is not shown, the third ventilation duct part 48 formed in the body 12 is in flow communication with the second ventilation duct part 32 in the body 12 via the fifth ventilation duct part 54 in the closing element 18.

In accordance with the uninterrupted arrow B, air from the environment can thus enter the cavity 30 laterally via the four ventilation duct parts 48, 54, 32, 34 after having passed through the sterile air filter 40.

As on the one hand the ventilation below the membrane filter is thus ensured and on the other hand a still existing negative pressure of the suction device cannot exert any attractive force on the membrane filter, the membrane filter can be lifted off the filtration base 16 in the "stop" position without any difficulty.

It should be noted that the three switching positions of the connection means 10 are reached simply by rotating the closing element 18, without the need for an additional valve or the like. All flow communications or interruptions in the suction duct and in the ventilation duct required for the respective operating mode are established by appropriately arranged duct parts in the rotatable closing element 18.

LIST OF REFERENCE NUMBERS 10 connection means
12 body
14 support
16 filtration base
18 closing element
20 operating element
22 latching element
24 latching recesses
26 first suction duct part in the body
28 second suction duct part in the support
30 cavity
30a collecting part of the cavity
32 second ventilation duct part in the body
34 first ventilation duct part in the support
34a intake of the first ventilation duct part
36 cavity
38 O-rings 40 sterile air filter
42 inlet of the sterile air filter
44 outlet of the sterile air filter
46 third suction duct part in the closing element
48 third ventilation duct part in the closing element or body
50 fourth suction duct part in the closing element
52 fourth ventilation duct part in the closing element
54 fifth ventilation duct part in the closing element
A direction of suction
B direction of ventilation

The invention claimed is:

1. A connection means for a suction device for vacuum membrane filtration applications, comprising:
   a support for receiving a membrane filter or a filtration base,
   a cavity formed below the membrane filter or the filtration base,
   a suction duct which opens centrally into the cavity, and
   a ventilation duct which opens laterally into the cavity,
   the connection means further comprising a closing element which can be moved into a plurality of switching positions and which can block or unblock both the suction duct and the ventilation duct depending on the switching positions,
   wherein the ventilation duct is separated from the suction duct in each of the plurality of switching positions.

2. The connection means according to claim 1, characterized in that the ventilation duct opens into the cavity via a collecting part of the cavity.

3. The connection means according to claim 1, characterized in that the closing element has both at least one suction duct part for completing the suction duct in at least one of the plurality of switching positions and at least one ventilation duct part for completing the ventilation duct in at least one of the plurality of switching positions.

4. The connection means according to claim 1, characterized in that in a first switching position of the plurality of switching positions, the suction duct is unblocked and the ventilation duct is blocked.

5. The connection means according to claim 4, characterized in that in a second switching position of the plurality of switching positions, both the suction duct and the ventilation duct are unblocked.

6. The connection means according to claim 5, characterized in that in a third switching position of the plurality of switching positions, the suction duct is blocked and the ventilation duct is unblocked.

7. The connection means according to claim 1, characterized in that the closing element is rotatably mounted in a body of the connection means, into which the support is also inserted.

8. The connection means according to claim 7, characterized in that at least the body is made of stainless steel or aluminum and is firmly or detachably connected to a suction device.

9. The connection means according to claim 7, characterized in that the closing element is detachably mounted in the body.

10. The connection means according to claim 1, characterized in that the ventilation duct has a ventilation duct part in a body of the connection means and a ventilation duct part in the support, which are in flow communication with each another via a sealed cavity formed substantially annularly between the body and the support.

11. The connection means according to claim 1, characterized in that the closing element is a plug of a stop-cock.

12. The connection means according to claim 1, characterized in that the closing element is mechanically coupled to an operating element.

13. The connection means according to claim 1, characterized by a latching mechanism by means of which the closing element is held in the respective switching position.

14. The connection means according to claim 1, characterized in that a sterile air filter is connected upstream of the ventilation duct.

15. A connection means for a suction device for vacuum membrane filtration applications, comprising:
   a support for receiving a membrane filter or a filtration base,
   a cavity formed below the membrane filter or the filtration base,
   a suction duct which opens centrally into the cavity, and
   a ventilation duct which opens laterally into the cavity,
   the connection means further comprising a closing element which can be moved into a plurality of switching positions and which can block or unblock both the suction duct and the ventilation duct depending on the switching position,
   wherein, in a first switching position of the plurality of switching positions, the suction duct is unblocked and the ventilation duct is blocked, and in a second switching position of the plurality of switching positions, both the suction duct and the ventilation duct are unblocked,
   wherein two suction duct parts are formed in the closing element, one of which completes the suction duct in the first switching position and the other completes the suction duct in the second switching position.

16. A connection means for a suction device for vacuum membrane filtration applications, comprising:
   a support for receiving a membrane filter or a filtration base,
   a cavity formed below the membrane filter or the filtration base,
   a suction duct which opens centrally into the cavity, and
   a ventilation duct which opens laterally into the cavity,
   the connection means further comprising a closing element which can be moved into a plurality of switching positions and which can block or unblock both the suction duct and the ventilation duct depending on the switching position,
   wherein, in a first switching position of the plurality of switching positions, the suction duct is unblocked and the ventilation duct is blocked, in a second switching position of the plurality of switching positions, both the suction duct and the ventilation duct are unblocked, and in a third switching position of the plurality of switching positions, the suction duct is blocked and the ventilation duct is unblocked,
   wherein two ventilation duct parts are formed in the closing element, one of which completes the ventilation duct in the first switching position and the other completes the ventilation duct in the third switching position.

* * * * *